(12) United States Patent
Herman

(10) Patent No.: US 7,655,668 B1
(45) Date of Patent: Feb. 2, 2010

(54) COMPOSITION AND METHOD FOR TREATMENT OF WARTS

(76) Inventor: Craig Herman, 126 Main St., Conrad, IA (US) 50621

( * ) Notice: Subject to any disclaimer, the term of this patent is extended or adjusted under 35 U.S.C. 154(b) by 843 days.

(21) Appl. No.: 11/037,403

(22) Filed: Jan. 18, 2005

(51) Int. Cl.
*A01N 43/54* (2006.01)
*A61K 31/505* (2006.01)
*A01N 37/36* (2006.01)
*A61K 31/60* (2006.01)
*A01N 45/00* (2006.01)
*A61K 31/56* (2006.01)

(52) U.S. Cl. .................. 514/274; 514/159; 514/171

(58) Field of Classification Search ............... 514/274
See application file for complete search history.

(56) References Cited

U.S. PATENT DOCUMENTS

2003/0072814 A1 * 4/2003 Maibach et al. ............. 424/722

* cited by examiner

*Primary Examiner*—Sreeni Padmanabhan
*Assistant Examiner*—Samira Jean-Louis

(57) ABSTRACT

Provided is a composition that includes 5-FU and salicylic acid. This composition is useful as a treatment for warts. As opposed to conventional compositions and methods, this composition need only be applied once a day. Also provided are methods for the preparation and use of the composition for treatment of warts.

5 Claims, No Drawings

COMPOSITION AND METHOD FOR TREATMENT OF WARTS

FIELD OF THE INVENTION

Embodiments of the present invention relate generally to compositions and methods for treating warts on an individual, and more particularly to a sustained release composition so that the composition need only be applied once a day.

BACKGROUND OF THE INVENTION

The present invention relates to a composition for treating warts including, but not limited to, common warts, plantar warts, flat warts, and filiform warts. The present invention is not to be limited to treating plantar warts. However, as a manner of convenience and to explain some of the types of problems that the present invention addresses, problems associated with the current modalities of plantar warts are discussed.

Plantar warts are epidermal lesions caused by an infection by the human papilloma virus (HPV), a double-stranded DNA virus. HPV has over a 100 subtypes, but those most found in plantar warts are HPV 1, 2, 4, and 10. Plantar warts are generally benign and usually self-limiting lesions, but are often painful and can be debilitating. The incidence of plantar warts is 1 to 2 percent in the general population, with 60% of cases resolving spontaneously within a two year period. Although multiple treatments have been proposed over the years, to date there is no uniformly effective treatment for warts.

Aggressive treatments for the recalcitrant wart include surgical excision, laser, and cryotherapy treatments. Because these approaches are often painful and do not guarantee success, doctors and patients may opt for a less invasive treatment, or patients may try to treat themselves at home.

The most common at home treatment for warts is a non-prescription salicylic acid preparation, usually a gel or cream, containing concentrations ranging from 10-60% salicylic acid. Salicylic acid acts in a catalytic manner breaking down protein (keratin) found in the wart and the thick layer of dead skin on top of the wart. To be effective, these preparations need to be applied several times a day over a series of weeks, even months. As such, efficacy is dependent on patient compliance with repeated applications. Even with patient compliance, less than half who use salicylic acid experience success. Therefore, alternative treatments have been proposed.

Several topical preparations are known in the art for use in the treatment of warts. As already noted, known treatments are disadvantageous in that they typically require repeated daily applications. Further, with many of these treatments, the patient needs to debride the wart between applications to provide maximum contact and penetration of the medication to the wart.

U.S. Pat. No. 6,599,513 is directed to emulsion formulations that are disclosed as optionally including various anti-psoriasis actives. These formulations require the presence of substantially intact oil bodies derived from a cell.

U.S. Patent Pub. No. 2003/0235627 to Maibach is directed to a wart treatment composition, and identifies 5-FU and salicylic acid as individual agents that have been tried in the past for the treatment of warts, but are disadvantageous due to potential damage to healthy skin and potential toxicity, respectively. Maibach requires topical delivery of its active ingredients in a basic carrier (i.e. pH of 7.5 to 13.0), as a strategy for enhancing the permeability of skin or mucosal tissue to the active agent.

Another home remedy for the treatment of warts is duct tape. Unlike most wart treatments, duct tape does not require repeated daily applications and works simply by occluding the wart, thereby creating a macerating and keratolytic environment. However, duct tape alone may not provide resolution of warts.

For these and other reasons, there is a need for the present invention.

Accordingly, it is an object of the present invention to provide a composition effective for the treatment of warts.

Another object of the present invention is to provide a composition effective for the treatment of warts that requires only once daily application.

Still another object of the present invention is to provide a method using a composition that is effective in the treatment of warts.

A further object of the present invention is to provide a kit effective for the treatment of warts that comprises a composition containing 5-FU and salicylic acid.

The method and means of accomplishing each of the above objectives as well as others will become apparent from the detailed description of the invention which follows hereafter.

SUMMARY OF THE INVENTION

The invention is based upon the observation that a composition of the combination of 5-FU and salicylic acid in a pharmacologically accepted topical vehicle are effective in treating warts. Methods of treating a wart of an individual are provided. The wart treatment composition of this invention is acidic. A therapeutically effective amount of a composition comprising 5-FU and salicylic acid is topically applied to a wart on an individual. Also provided is a kit for treating a wart on an individual including a quantity of a composition comprising 5-FU and salicylic acid and an applicator. A method for the preparation of a composition of 5-FU and salicylic acid is provided.

DETAILED DESCRIPTION OF THE PREFERRED EMBODIMENT

As used herein, the "treatment" refers to any process, action, application, therapy, or the like, wherein an individual with a wart, is subject to the present invention with the object of improving the individual's condition, directly or indirectly.

As used herein, the term "therapeutically effective amount" means that amount of a composition of the present invention effective in reducing the size of a wart.

The present invention is directed to a pharmaceutical composition for the treatment of warts. The present inventors have discovered that the combination of 5-FU and salicylic acid in a gel-like vehicle is useful in treating warts. Accordingly, a method for administering the composition for treatment of warts is also encompassed by the invention. The composition of this invention is further distinguished from prior art wart treatments in allowing for once daily administration.

In accordance with preferred embodiments of the invention, there is provided a composition comprising 5-FU and salicylic acid, present in a therapeutically effective amount and in a pharmaceutically acceptable vehicle for topical treatment of warts. The 5-FU is typically present in an amount ranging from about 0.5 to 5.0% by weight of the composition. The salicylic acid is typically present in an amount ranging from about 10.0 to 25.0% by weight of the composition. The concentrations of these drugs may vary from these ranges due to a variety of factors, including size and location of the wart, weight and age of the patient, cost, etc.

Without wishing to be bound by any specific theory, it is believed that the 5-FU and salicylic acid of the invention act in a synergistic manner to provide the desired resolution of a wart. Together, the salicylic acid removes the keratin of the wart and surrounding skin to improve penetration of the 5-FU, which inhibits viral replication of the HPV which causes wart formation. The synergistic effect provides a composition for treating warts that is superior to using either 5-FU or salicylic acid alone.

In contrast to other known treatments, the composition need only be applied daily for the treatment of warts. It is believed that the composition is capable of sustained release throughout the day. In accordance with principles of Fickian diffusion, as the composition dries and the concentration of active ingredients increase, the better the penetration of active ingredients into the treatment site.

In addition to the 5-FU and salicylic acid, the composition may additionally include an organic solvent, an adhesive, plasticizer, and a water swellable polymer. The organic solvent may be one or more of dimethylsulfoxide (DMSO), N,N'-dimethylacetamide (DMA), N'N'-dimethylformamide (DMF), dioxane, tetraglycol, or the like. DMSO is preferred in this respect. The solvent should be present in a concentration sufficient to dissolve the 5-FU, but is typically present in a concentration ranging from about 5-50% by weight, with about 15-25% by weight being preferred and about 20% by weight being most preferred since this concentration provides a good consistency. Other concentrations may be preferred, however, depending on the consistency desired, i.e. the more solvent added, the thinner the composition becomes and vice versa.

Appropriate adhesives for use in the invention include, but are not limited to, polyvinyl alcohol, polyethylene oxides, polyethylene glycols of molecular weight 3350 and higher, hydroxypropylcellulose, and povidone. Polyvinyl alcohol is preferred. The adhesive is typically present in an amount from about 10 to 75% by weight, preferably about 45-55% by weight, and most preferably about 50% by weight of the composition. This latter concentration is preferred since it provides a good consistency. Again, however, more or less adhesive may be included depending on the consistency desired, i.e. the more adhesive added, the thicker the composition and vice versa.

The composition may optionally include a plasticizer. Suitable plasticizers are typically high-boiling, water-soluble organic compounds containing hydroxyl, amide, or amino groups. Such plasticizers include, but are not limited to, soy, egg or synthetic lecithin, ethylene glycol, tetraethylene, hexamethylene, nonaethylene glycol, formamide, ethanolamine salts, water, glycerin, or combinations thereof, with lecithin being a preferred plasticizer. Such plasticizers are well known in the art. It is believed that the plasticizer serves the dual roles of a penetration enhancer for the active ingredients, as well as enhancing the flexibility of the adhesive. A plasticizer is therefore preferably included in the formulation to provide these benefits. The plasticizer is typically present in the composition in an amount ranging from about 0.4-2.0% by weight, with about 1-2% by weight being preferred, and about 0.9% by weight being most preferred.

The composition may also include a water swellable polymer which acts as an extender, and serves to thicken the composition. Such water swellable polymers are well known in the art and include, but are not limited to, microcrystalline cellulose, hydroxypropyl cellulose, hydroxypropyl methylcellulose, methyl cellulose, methyl ethyl cellulose, sodium carboxymethylcellulose, gums, carboxyvinyl polymer, hydroxyethyl cellulose, cornstarch, casein, urea, dextrin, and fume silica. The filler is typically present in an amount from about 1-10% by weight, preferably about 3-6% by weight, with about 4.67% by weight being most preferred. It should be understood that the water swellable polymer constitutes the remainder of a given composition after other ingredients and their respective amounts are determined.

The ingredients of this invention when combined form topical adhesive gels. These gels, while clear, may optionally include some amounts of precipitated active ingredient. The presence of this precipitated drug does not interfere with the activity of the compositions in treating warts. Unlike the compositions of U.S. Pat. No. 6,599,513, the compositions of the present invention do not require the use of substantially intact oil bodies and, in fact, may be substantially free of intact oil bodies. As used herein, the term "substantially free of intact oil bodies" means the composition contain insufficient amounts of intact oil bodies so as to create an emulsion.

The ingredients can all be combined together to form a workable composition. In a preferred method of manufacture, the 5-FU is first combined with the solvent so as to dissolve the 5-FU. Salicylic acid is then added, followed by the remaining ingredients.

The compositions of the invention may further include a variety of substances, including suitable stabilizers, buffers, thickeners, lubricants, wetting, and dissolving agents as well as colorings, moisturizers, preservatives, and fragrances. These minors are added in small amounts and are conventionally known in pharmaceutical formulation work to enhance elegance. Such minors should comprise less than about 1% of the overall composition.

Other actives may also be used in this invention so long as they are safe for external use and compatible with the other ingredients in the formulation. Examples of such actives include, but are not limited to, antibiotics, antivirals, anti-inflammatories, antioxidants, analgesics, etc.

The present invention is further directed to a method of treating warts. The method of the invention comprises topically applying to a wart on an individual a therapeutically effective amount of the compositions of the invention. The composition may be applied using an applicator, for example, a swab, sponge, finger cot or a toothpick. In one embodiment of the method, the composition is applied using the side of a flat toothpick to "frost" the wart. While the compositions of this invention are adhesive in and of themselves, in another embodiment of the invention, the method further comprises occluding the wart with an occluding agent to aid the composition's absorption into the wart, protect the composition from rubbing off, and also further keratolytic activity. Many occluding agents are known to those skilled in the art. These include, but are not limited to, bandages, plastic wrap, and adhesive tape, for example, duct tape.

When applied, the compositions are wet, but soon dry to form a film. Unlike prior art wart treatments, the compositions of this invention need only be applied once a day to achieve therapeutic results. However, the composition is safe for application multiple times a day if the patient so chooses, although no therapeutic or cost benefit is achieved by doing so. For best results, the wart treatment composition of this invention is applied once daily at approximately the same time each day. The present inventor has surprisingly found that applying the composition at bedtime rather than in the morning provides even better therapeutic results. The treatment site is preferably washed with mild soapy water and dried prior to reapplication. Daily applications should preferably continue for a period of time of at least one week, or until the patient can no longer visualize the wart. This latter time period will vary greatly based on the size of the wart.

The following examples are offered to illustrate but not limit the invention. Thus, it is presented with the understanding that various formulation modifications as well as method of delivery modifications may be made and still are within the spirit of the invention.

EXAMPLE 1

Wart Treatment Composition

| Ingredient | Quantity (in grams) |
| --- | --- |
| Polyvinyl (PVA) alcohol powder | 12.00 |
| Edetate disodium USP (dihydrate) powder | 0.05 |
| Lecithin soya granules | 1.80 |
| Water paraben preserved liquid | 100.00 |

Manufacturing Procedure:

1. Disperse PVA powder and EDTA in room temperature water for ½ hour under moderate stir speed using a magnetic stir bar.
2. Heat the dispersion to 80° C. and continue mixing until all globules have dissolved.
3. Discontinue heat, but continue stirring on the plate until a clear gel solution forms. This may require sitting at room temperature to eliminate the air bubbles. Once the gel is moderately warm (not hot), disperse the lecithin with stirring until a uniform dispersion forms.

The resulting compound has a pH of 5.05.

EXAMPLE 2

Wart Treatment Composition

| Ingredient | Quantity |
| --- | --- |
| 5-fluorouracil granules | 2.00 g |
| Salicylic acid powder | 17.00 g |
| DMSO liquid | 20.00 ml |
| Microcrystalline cellulose NF (PH-105) powder | 4.66667 g |
| PVA-LS (12/18.8)% gel | 100.00 g |

Manufacturing Procedure:

1. Take an appropriately sized beaker with a plastic stir rod.
2. Add a magnetic stir bar, DMSO and 5-fluorouracil, stir until completely dissolved.
3. Add salicylic acid and let dissolve, then remove magnetic stir bar.
4. Add ½ total weight of PVA-LS, and stir with rod.
5. Add Avicel pH-105 and stir.
6. QS with PVA-LS to final volume and stir well The resulting compound has a pH of 2.70.

EXAMPLE 3

Polyvinyl Alcohol 10% Gel

| Ingredient | Quantity |
| --- | --- |
| Polyvinyl alcohol powder | 10.00 g |
| Edetate disodium USP (dihydrate) powder | 0.05 g |
| Water paraben preserved liquid | 100.00 ml |

The resulting compound has a pH of 4.87.

Manufacturing Procedure:

1. Disperse PVA powder in room temperature water for ½ hour under moderate stir speed using a magnetic stir bar.
2. Heat the dispersion to 60-80° C. and continue stirring for another ½ hour.
3. Discontinue heat, but continue stirring on the plate until clear gel solution forms.

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A composition for treatment of warts consisting of: from 0.5 to 5.0% by weight 5-fluorouracil (5-FU); from 10.0 to 25.0% by weight salicylic acid; from 5 to 50% by weight of DMSO; from 1-10% by weight of a water-swellable polymer; and from 10-75% by weight of an adhesive; whereby the composition is a sustained release topical gel that releases salicylic acid onto the wart for removal of keratin of the wart and surrounding skin to allow penetration of the 5-FU into the wart.

2. A composition for treatment of warts consisting of: from 0.5 to 5.0% by weight 5-fluorouracil (5-FU); from 10.0 to 25.0% by weight salicylic acid; from 5 to 50% by weight of DMSO; from 1-10% by weight of a water-swellable polymer; and 10-75% by weight of an adhesive; whereby the composition is a sustained release topical gel that releases salicylic acid onto the wart for removal of keratin of the wart and surrounding skin to allow penetration of the 5-FU into the wart.

3. A composition for treatment of warts consisting of: from 0.5 to 5.0% by weight 5-fluorouracil (5-FU); from 10.0 to 25.0% by weight salicylic acid; from 5 to 50% by weight DMSO; from 0.4 to 2.0% by weight lecithin; from 1-10% by weight of a water-swellable polymer; and 10-75% polyvinyl alcohol gel that releases salicylic acid onto the wart for removal of keratin of the wart and surrounding skin to allow penetration of the 5-FU into the wart.

4. A composition for treatment of warts consisting of: 2% by weight 5-fluorouracil (5-FU); 17% by weight salicylic acid; from about 5 to 50% by weight of DMSO; from about 1-10% by weight of a water-swellable polymer; and 10-75% by weight of an adhesive; whereby the composition is a sustained release topical gel that releases salicylic acid onto the wart for removal of keratin of the wait and surrounding skin to allow penetration of the 5-FU into the wart.

5. A composition for treatment of warts consisting of: from 2-5% by weight 5-fluorouracil (5-FU); from 10-25% by weight salicylic acid; from 5 to 50% by weight of DMSO; from 1-10% by weight of a water-swellable polymer; and 10-75% by weight of an adhesive; whereby the composition is a sustained release topical gel that releases salicylic acid onto the wart for removal of keratin of the wart and surrounding skin to allow penetration of the 5-FU into the wart.

* * * * *